United States Patent [19]

Albright

[11] 4,133,846
[45] Jan. 9, 1979

[54] HYDROXYL CONTAINING PHOSPHATES AND POLYPHOSPHATES

[75] Inventor: James A. Albright, Ann Arbor, Mich.

[73] Assignee: Velsicol Chemical Corporation, Chicago, Ill.

[21] Appl. No.: 811,491

[22] Filed: Jun. 30, 1977

[51] Int. Cl.$^2$ ............................................. C07F 9/11
[52] U.S. Cl. ................................. 260/928; 260/953; 521/107; 521/906; 521/169; 260/45.7 P; 528/72; 528/287
[58] Field of Search ............................... 260/928, 953

[56] References Cited

U.S. PATENT DOCUMENTS

| 3,321,555 | 5/1967 | Lutz et al. | 260/928 X |
| 3,830,886 | 8/1974 | Davis et al. | 260/953 OR |

FOREIGN PATENT DOCUMENTS 2506599  8/1975  Fed. Rep. of Germany ........... 260/928

Primary Examiner—Anton H. Sutto
Attorney, Agent, or Firm—Robert M. Phipps; Howard J. Greenwald

[57] ABSTRACT

Novel esters of pentavalent phosphorus acid having the formula

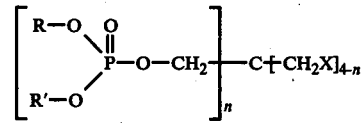

wherein R and R' are haloalkyl containing from 2 to 6 carbon atoms and from 1 to 6 halogen atoms; n is an integer of from 1 to 3; each X is independently selected from hydrogen, halogen, alkyl, or hydroxyl, provided that at least one X is hydroxyl. The above compounds are effective reactive flame retardants in polyurethane and polyester polymeric compositions.

7 Claims, No Drawings

HYDROXYL CONTAINING PHOSPHATES AND POLYPHOSPHATES

BACKGROUND OF THE INVENTION

1. Field of the Invention

This invention pertains to certain novel esters of pentavalent phosphorus acid and to plastic compositions containing these esters as flame retardants therefor.

2. Description of the Prior Art

During the past several years, a large number of flame retardants have been developed for use with an almost equally large number of flammable materials. Cellulosic materials such as paper and wood and polymeric materials such as polyolefins, polyesters, polyurethane and polystyrene are just two examples of materials for which flame retardants have been developed. For any class of flammable materials, such as synthetic type polymers, those skilled in the art have long been aware that some flame retardant additives are more effective in polymers and polymeric compositions than other flame retardant additives. This is because the efficacy of any flame retardant in polymers or polymeric compositions is measured not only by the flame retardant capability of the additive but also by the ability of the additive to improve or modify, or at least not to detract from, other physical or mechanical properties of the polymer or polymeric composition. The mere fact, therefore, that most flame retardants contain halogen and phosphorus atoms does not assure that any given halogenated or phosphorus-containing compound will impart usable flame retarding characteristics to all or even to any polymeric system. Furthermore, as those skilled in the art have improved the flame retardancy of many polymeric materials, they have been simultaneously required to provide the necessary flame retardancy with a minimal effect upon other properties of the polymer such as the light stability, processability, and flexural, tensile and impact strengths. Also, it has been the desire of those involved in the art of flame retardants to provide flame retardants having a durable lasting effect. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

The prior art considered in the preparation of the instant application includes U.S. Pat. Nos. 3,132,169 to Birum et al., 3,324,205 to Carpenter et al., 3,385,801 to Birum et al., 3,391,226 to Birum et al., 3,433,856 to Friedman, 3,471,592 to Friedman, 3,781,388 to Jenkner et al., 3,830,886 to Davis et al., and German Pat. No. 2,416,663 to Burke.

In particular, U.S. Pat. No. 3,132,169 to Birum et al. discloses flame retardant esters of pentavalent phosphorus acids, which esters contain both chlorine and bromine, and which are selected from the class consisting of a phosphate of the general formula

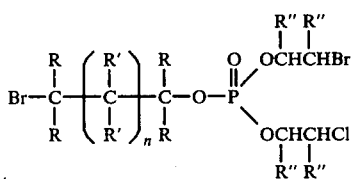

wherein R is selected from the class consisting of hydrogen, alkyl and haloalkyl radicals of from 1 to 2 carbon atoms, R' is selected from the class consisting of hydrogen, alkyl and haloalkyl radicals of from 1 to 5 carbon atoms, R" is selected from the class consisting of R' and hydrocarbyloxymethyl radicals of from 1 to 8 carbon atoms, wherein one R" at a pair of adjacent carbon atoms must be hydrogen, and n is an integer from 0 to 1.

U.S. Pat. No. 3,781,388 to Jenkner et al. discloses flame-proofing agents having the general formula

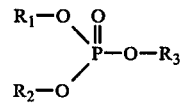

wherein $R_1$ is a halogen-containing alkyl radical containing 2 to 4 carbon atoms and 1 to 3 halogen atoms; $R_2$ is an alkyl radical containing 2 to 4 carbon atoms which may also optionally contain at least one halogen atom and/or at least one OH group; and $R_3$ is an alkyl group containing 2 to 4 carbon atoms and one OH group.

U.S. Pat. No. 3,830,886 to Davis et al. discloses flame retardant additives of the general formula

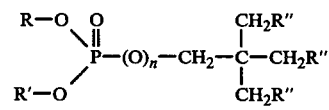

wherein n is zero or one; R is a lower alkyl, phenyl or alkylated phenyl having one to three lower alkyl substituents, R' is R or

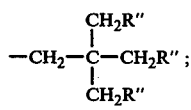

and at least one R" is Br or Cl and each remaining R" is OH, Br, or Cl.

Birum et al. does not disclose that the compounds therein can contain hydroxyl substituents attached to the neopentyl group. As those skilled in the art of flame retardants know, the indiscriminate substitution of a hydroxyl group for a halogen or hydrogen atom of a compound will often result in a dramatic decrease in the modified hydroxy substituted compound's hydrolytic and thermal stability. However, by the use of a high degree of inventive skill, it was possible to effectuate a substitution of a hydroxyl group for a halogen or hydrogen atom and still maintain the basic physical properties of the nonhydroxyl-containing compound. The net result of this inventive skill is that one now can produce a reactive flame retardant capable of reactively being bound into a polymer chain, e.g., polyurethane and polyester, and thereby reducing the migration of the flame retardant and the subsequent flame retardancy loss of the polymeric composition. This result has long been sought after and much desired in the art of flame retardants.

Davis et al. discloses triesters of phosphorus acid in which one of the ester groups is a lower alkyl group. Davis et al. state that "prior art fire-retardants suffer from a number of disadvantages such as their tendency to produce hydrogen halides such as HBr when heated" and that the "new compounds (of their invention) have unusual resistance to thermal and hydrolytic decomposition and are therefore superior fire-retardant additives for wood, textiles, plastics, and the like." Davis et al, appear to have acheived this unusual hydrolytic stability by using groups having no hydrogen containing carbon atoms in a beta position relative to halogen bearing carbon atoms.

Applicant has found, contrary to the teachings of the prior art, that the instant compounds possess unusual hydrolytic stability despite the fact that they may possess halogen atoms adjacent to the beta carbon atoms.

Jenkner et al. disclose phosphates containing two haloalkyl groups of from 2 to 4 carbon atoms and a single hydroxyalkyl group of from 2 to 4 carbon atoms. These phosphates, however, are thermally and hydrolytically less stable, and therefore less useful than applicant's instant compounds.

SUMMARY OF THE INVENTION

In accordance with this invention there are provided esters of pentavalent phosphorus acid of good thermal and hydrolytic stability having the formula

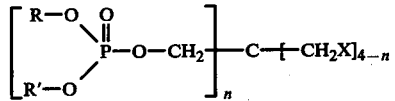
(I)

wherein R and R' are haloalkyl containing from 2 to 6 carbon atoms and from 1 to 6 halogen atoms; n is an integer from 1 to 3; each X is independently selected from hydrogen, halogen, alkyl, or hydroxyl, provided that at least one X is hydroxyl. Also polyurethane or polyester polymeric compositions comprising a polyurethane or polyester polymer and a flame retarding amount of the above described compounds are provided.

DESCRIPTION OF THE PREFERRED EMBODIMENTS

Compounds within the scope of this invention have formula I above. Each X is independently selected from hydrogen, hydroxyl, alkyl containing 1 to about 4 carbon atoms and halogen, preferably chlorine or bromine, provided that at least one X is hydroxyl, R and R' are lower haloalkyl groups containing from 2 to 6 carbon atoms and 1 to 6, preferably 1 to 3, halogen atoms, preferably chlorine or bromine. The haloalkyl groups can be branched or straight chain lower haloalkyl groups. Straight chain lower haloalkyl groups are preferred. Compounds of Formula I, wherein X is independently selected from hydrogen, halogen, preferably chlorine or bromine, or hydroxyl, provided that at least one X is hydroxyl, are preferred, with said compounds wherein n > 1 being more preferred. For purposes of illustration only, Table I above is designed to further help describe the compounds of formula I and is neither meant nor should it be taken to be a complete listing of all the compounds within the scope of this invention.

TABLE I

| Compound | X | X | X | R | R' | n |
|---|---|---|---|---|---|---|
| 1 | —OH | —H | —H | 2,3-dibromopropyl | 2,3-dibromopropyl | 1 |
| 2 | —OH | —H | —Br | 2-bromoethyl | 2-chloro-3-bromopropyl | 1 |
| 3 | —OH | —Br | —Br | 3-bromopropyl | 3-bromobutyl | 1 |
| 4 | —OH | —OH | —OH | 2,3-dichlorobutyl | 2-bromoethyl | 1 |
| 5 | —OH | —Br | —Br | 2,3-dibromopropyl | 2,3-dibromopropyl | 1 |
| 6 | —OH | —Cl | —H | 2-bromoethyl | 2,3-dichloropropyl | 1 |
| 7 | —OH | —OH | —H | 2,3-dibromopropyl | 2,3-dibromopropyl | 1 |
| 8 | —OH | —H | —H | 2,4,4-tetrachlorobutyl | 2,4,4-tetrachlorobutyl | 1 |
| 9 | —OH | —H | —H | 2,3-dichloropropyl | 2,3-dichloropropyl | 1 |
| 10 | —OH | —H | —H | 2-chloroethyl | 2-chloroethyl | 1 |
| 11 | —OH | —H | —H | 1,3-chloro-2-propyl | 1,3-dichloro-2-propyl | 1 |
| 12 | —OH | —OH | —Cl | 2,3-dibromopropyl | 2,3-dibromopropyl | 1 |
| 13 | —OH | —OH | — | 2-chloroethyl | 2-chloroethyl | 2 |
| 14 | —OH | —OH | —CH$_3$ | 2,3-dibromopropyl | 2,3-dibromopropyl | 1 |
| 15 | —OH | — | — | 2-chloroethyl | 2-chloroethyl | 3 |

Compounds within the scope of this invention are prepared according to the general reaction scheme:

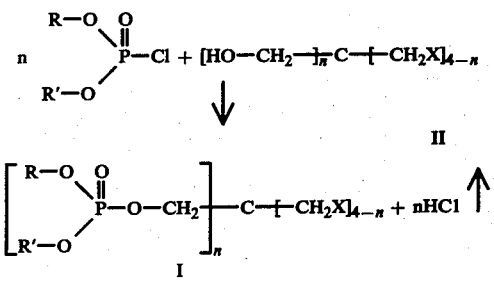

wherein X, R and R' are as defined above. In general, n moles of the desired haloalkyl chlorophosphate and 1 mole of compound II are reacted under conditions such that they co-react to form compounds of formula I. Generally reaction temperatures range from about 20° to about 120° C. The reaction can be carried out in the presence or absence of a solvent. If a solvent is used it should preferably be an inert organic solvent. Exemplary solvents include benzene, toluene, and chloroform. Catalytic quantities of a metal salt or oxide such as magnesium oxide, magnesium chloride, calcium oxide, calcium chloride, titanium chloride, or vanadium acetate, or stoichiometric quantities of an organic base such as pyridine or triethylamine can be used.

Depending on the physical condition of the final end product various product purification and isolation procedures can be used. In the case of a liquid final product, said liquid product is washed with aqueous ammonia to remove any residual acidity. The aqueous ammonia wash is followed by a water wash. The washed product is dreid by standard techniques, e.g., at a temperature of from about 100° to about 130° C. until constant weight is achieved.

When a solid product is attained, said solid product can be purified by washing or recrystallization by techniques which are well known to those skilled in the art, e.g., the solid product can be washed with water or organic solvents such as benzene, toluene, methanol, ethanol, etc., or crystallized from said solvent. The purified solid product is then dried by standard techniques, e.g., at a temperature from about 50° to about 150° C. until constant weight is achieved.

The hydroxyl containing esters of pentavalent phosphorus acid of this invention as well as mixtures thereof are useful as reactive flame retardants in polymeric compositions selected from the group consisting of polyurethane, including flexible and rigid foams and elastomers, and polyester, both saturated and unsaturated polyester, including styrenated polyester. A detailed description of the polyurethane and polyester polymeric compositions capable of being used with the flame retardants of formula I can be found in Modern Plastics Encyclopedia, Vol. 52, No. 10A, McGraw-Hill, Inc., New York, N.Y. (1975), said Encyclopedia being incorporated herein by reference.

Generally the term polyurethanes means polymers containing repeated urethane linkages

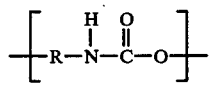

where R is aromatic or aliphatic group. These polymers are generally made by reacting a polyisocyanate with a compound having a plurality of active hydrogens (i.e., a compound having active hydrogen and which gives a positive Zerewitinoff test).

Thus the polyurethanes used in the present invention compositions are any polyurethane herein defined which one so desires to flame retard. It is to be understood that the polyurethanes used can be a "virgin" material, i.e., substantially free of additives such as stabilizers, plasticizers, dyes, pigments, fillers, and the like or the polyurethanes can have additives (such as those mentioned and described herein).

Generally the term polyesters means polycondensate products of the reaction of dibasic acids and/or anhydrides or derivatives therefrom with dihydroxy alcohols. This term includes both saturated and unsaturated polyesters. Unsaturated polyesters are so designated where part or all of the respective acids, anhydrides and/or alcohols contain crosslinkable ethylenic bonds.

Examples of dibasic acids and anhydrides include, without limitation, phthalic anhydride, maleic anhydride, fumaric acid, tetrahydrophthalic anhydride, tetrachlorophthalic anhydride, tetrabromophthalic anhydride, 1,4,5,6,7,7-hexachlorobicyclo-(2,2,1)-5-heptene-2,3-dicarboxylic acid, i.e., chlorendic acid, isophthalic acid and terephthalic acid.

Examples of dihydroxy alcohols include, without limitation, ethylene glycol, diehtylene glycol, propylene glycol, butane glycol, butene diol, hexane diol, hexene diol, butyne diol, cyclohexane diol, cyclohexene diol, neopentyl glycol, hydrogenated bisphenol A, 2,2,4-trimethyl-1,3-pentanediol and 1,4-cyclohexanedimethanol.

This term also includes copolymers of polyesters which are resins derived from reactants used to give polyester resins and reactants used to give other polycondensate linkages. For example, there may be mentioned the reaction of dibasic anhydrides with dihydroxy alcohols and diamines to give polyester and polyamide links along the same molecular backbone. Also, those products formed by addition polymerization of reactants with ethylenic linkages before or after the polyester condensation reaction. For example, the addition reaction of styrene with unsaturation in polyesters after polycondensation or the formation of an additional polymer with carboxylic acid or other condensable end-groups for further polymerization by polyesterification.

Thus the polyesters used in the present invention compositions is any polyesters herein defined and which one so desired to flame retard. It is to be understood that the polyesters used can be a "virgin" material, i.e., substantially free of additives such as stabilizers, plasticizers, dyes, pigments, fillers, and the like or the polyesters can have additives (such as those mentioned and described herein).

It is an advantage of this invention that the present flame retardants, since they contain a free hydroxyl group, can be reacted and chemically bound into the polyurethane polymer matrix if they are added, for example, along with the polyol employed in making the polyurethane, to provide permanent nonfugitive flame retardancy. If the neopentyl moiety of the compounds of formula I contains only one hydroxyl group, e.g., compound 1 in Table I, these compounds can be used to control the polymer chain growth as chain stoppers. If the neopentyl moiety contains a plurality of hydroxyl groups, e.g., compound 7 in Table I, these compounds can contribute to the overall increase in chain length and may even be used as the sole polyol reactant to coreact with the toluene diisocyanate to form the polyurethane. Likewise, the present flame retardants of formula I can be reacted and chemically bound into the polyester matrix if they are added, for example, along with the diol employed in making the polyester, to provide permanent non-fugitive flame retardancy. If the neopentyl moiety of the compounds of formula I contains only one hydroxyl group these compounds can generally be used to control the polymer chain growth as chain stoppers. If the neopentyl moiety contains a plurality of hydroxyl groups these compounds can generally contribute to the overall increase in chain length and may even be used as the sole diol reactants to coreact with the diacids or anhydrides to form the polyesters.

Being bound into, or reacted into, the matrix of the polymer the flame retardant phosphates of this invention are not subject to solvent extraction or migration due to difference in vapor pressure, reaction to sunlight or other chemical influences. Additionally because the flame retardants of this invention become an integral part of the polymer there is no significant change in physical properties such as is typically experienced by the use of additive type flame retardants, particularly when used in large amounts.

The flame retardants within the scope of this invention may additionally be incorporated into or applied onto the above polymers by techniques which are standard or known to those skilled in the art as described, for example, in J. M. Lyons, "The Chemistry and Use of Fire Retardants", Wiley Interscience, New York (1970) or Z. E. Jolles, "Bromine and Its Compounds", Academic Press, New York (1966).

The amount of flame retardant which is used in the compositions and in the methods of this invention is a flame retardant amount, i.e., that amount necessary to produce measurable flame retardancy in the compositions which are so modified. Depending upon the particular compound and the particular polymer with which it is combined, the quantity of flame retardant employed in the compositions and methods of this invention can generally be from about 0.5 to about 50 percent or more by weight of the total composition. Generally, for most compositions, the flame retardant of the present invention will comprise from about 1 to about 25 percent by weight of the total composition.

In addition to the flame retardant compounds within the scope of this invention, the flame retardancy of a polymer such as polystyrene can be further enhanced through the use of so called "synergists" or enhancing agents which, when used with the compounds of formula I, promote a cooperative effect therebetween and thus enhance the flame retardancy of the resultant plastic composition as compared to the flame retardancy of either one component used separately. These "enhancing agents" comprise the oxides and halides of groups IVA and VA of the Periodic Table, and are further described in Modern Plastics Encyclopedia, ibid., as well as U.S. Pat. Nos. 2,993,924; 2,996,528; 3,205,196 and 3,878,165. Without limitation, preferred enhancing agents include $Sb_2O_3$, $SbCl_3$, $SbBr_3$, $SbI_3$, $SbOCl$, $As_2O_3$, $As_2O_5$, $ZnBO_4$, $BaB_2O_4 \cdot H_2O$, $2.ZnO.3B_2O_3.3.5-H_2O$ and stannous oxide hydrate. The more preferred enhancing agent is antimony trioxide. The enhancing agent can be employed in concentrations as high as 30 percent by weight of the total composition, preferably up to 15 percent, and more preferably up to 10 percent, by weight of the total composition. One level of synergist which is often used is an amount which is from about 25 to about 75 percent, preferably from about 33 to 67 percent, by weight of the flame retardant phosphates described above.

It is also within the scope of the present invention to employ other materials in the present invention compositions where one so desires to achieve a particular end result. Such materials include, without limitation, adhesion promoters, antioxidants, antistatic agents, antimicrobials, colorants, flame retardants such as those listed on pages 456–458, Modern Plastics Encyclopedia, ibid., (in addition to the new class of flame retardants described herein), heat stabilizers, light stabilizers, pigments, plasticizers, preservatives, ultraviolet stabilizers and fillers.

In this latter category, i.e., fillers, there can be mentioned without limitation, materials such as glass, carbon, cellulosic fillers (wood flour, cork and shell flour), calcium carbonate (chalk, limestone, and precipitated calcium carbonate), metal flakes, metallic oxides (aluminum, beryllium oxide, and magnesia), metallic powders (aluminum, bronze, lead, stainless steel and zinc), polymers (comminuted polymers and elastomer-plastic blends), silica products (diatomaceous earth, novaculite, quartz, sand, tripoli, fumed colloidal silica, silica aerogel, wet process silica), silicates (asbestos, kaolimite, mica, nepheline syenite, talc, wollastonite, aluminum silicate and calcium silicate), and inorganic compounds such as barium ferrite, barium sulfate, molybdenum sidulfide and silicon carbide.

The above mentioned materials, including fillers, are more fully described in Modern Plastics Encyclopedia, ibid., and which publication is incorporated herein by reference.

The amount of the above described materials employed in the present invention compositions can be any quantity which will not substantially adversely affect the desired results derived from the present invention compositions. Thus, the amount used can be zero (0) percent, based on the total weight of the composition, up to that percent at which the composition can still be classified as a plastic. In general, such amount will be from about zero percent to about 75 percent and specifically from about one percent to about 50 percent.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

Preparation of bis-(2,3-dibromopropyl)-2,2-dimethyl-3-hydroxypropyl phosphate (Compound 1 of Table I)

To a mechanically stirred solution of 516 grams of bis(2,3-dibromopropyl) chlorophosphate and 104 grams of neopentyl glycol is added 0.1 grams of magnesium oxide. The solution is heated slowly to 80° C. and held at that temperature for four hours until the hydrogen chloride evolution ceases. The reaction mixture is heated to 95° C. for one hour using an aspirator vacuum to remove residual hydrogen chloride. Upon cooling to 40° C., the reaction mixture is washed with aqueous ammonia and two additional times with water. Volatile impurities are removed by steam distillation. The product is dried, treated with Celite ®[1] and Celkate ®[2] and filtered. The structure of the resulting 495 grams of a clear light yellow liquid is confirmed by NMR and IR analysis.

[1] brand of diatomaceous earth filter aid.
[2] brand of magnesium silicate filter aid.

EXAMPLE 2

Preparation of bis-(2,3-dichloropropyl)-2,2-dimethyl-3-hydroxypropyl phosphate (Compound 9 of Table I)

To a mechanically stirred solution of 406 grams of bis-(2,3-dichloropropyl)chlorophosphate and 125 grams of neopentyl glycol was added 0.1 gram of magnesium oxide. The solution was slowly heated to 65° C. and held between 65° C. and 75° C. for seven hours until the hydrogen chloride evolution ceased. After cooling overnight, the product was washed with aqueous ammonia and two additional times with water. Volatile impurities were removed by steam distillation. The product was dried, treated with Celite and Celkate and filtered. The structure of the resulting 360 grams of a yellow liquid was confirmed by NMR and IR analysis.

EXAMPLE 3

Preparation of bis-(2,3-dibromopropyl)-2,2-bis(hydroxymethyl)-3-chloropropyl phosphate (Compound 12 of Table I)

To a mechanically stirred solution of 652 grams of bis-(2,3-dibromopropyl)chlorophosphate and 195 grams of chloropentaerythritol was added 0.1 grams of magnesium oxide. The solution was heated to 70° C. and held at this temperature for five hours. After cooling to 40° C., the product was washed with aqueous ammonia and two additional times with water. The product was dried, treated with Celite and Celkate and filtered. The structure of the resulting 754 grams of product was confirmed by NMR and IR analysis.

EXAMPLE 4

Preparation of tetrakis-(chloroethyl)pentaerythritol diphosphate (Compound 13 of Table I)

To a mechanically stirred solution of 282 grams of bis-(2-chloroethyl)chlorophosphate and 54.4 grams of pentaerythritol was added 0.1 grams of magnesium oxide. The solution was heated to 80° C. and held at that temperature for six hours until the hydrogen chloride evolution ceased. After cooling the solution to room temperature, the product was washed with aqueous ammonia and two additional times with water. The product was dried to a constant weight, treated with Celite and Celkate and filtered. The structure of the resulting 110 grams of a colorless liquid was confirmed by NMR and IR analysis.

EXAMPLE 5

A rigid polyurethane foam is prepared using the following basic formulation:

| Component | Parts per Hundred Parts Polyol (php) |
|---|---|
| Polyol[a] | 100 |
| Silicone Glycol Surfactant[b] | 2 |
| Trichlorofluoromethane[c] | 35 |
| Polyisocyanate[d] | 135 |

[a] alkanolamine polyol, molecular weight approximately 3500, hydroxyl number approximately 530, Thanol R-350-X, Jefferson Chemical Co., Houston, TX.
[b] Dow Corning 193, Dow Corning Corp., Midland, MI.
[c] Freon 11B, E. I. DuPont de Nemours & Co., Wilmington, DE.
[d] Polymeric aromatic isocyanate, 31.5% available, NCO, Mondur MRS, Mobay Chemical Co., Pittsburgh, PA.

The polyol, surfactant, and fluorocarbon blowing agent are combined in a masterbatch based on 1000 grams of polyol to minimize loss of blowing agent.

The following procedure is used to prepare the foam:
1. The polyisocyanate is weighed into a tared, 10 ounce, paper cup (allowances being made for holdup) and the cup set aside while the remaining ingredients are weighed out and mixed.
2. The polyol masterbatch is weighed out, in the proper amount to give 100 grams of polyol, in a one quart, untreated, paper cup.
3. The 10 grams of the flame retardant of Example 1 are then weighed into the same one quart cup.
4. The contents of the one quart cup are mixed at 1000 rpm for 5 seconds.
5. The polyisocyanate is then added and stirring at 1000 rpm continues for 10 seconds.
6. The mix is poured into a five-pound, untreated, paper tub and allowed to rise.

After the foam is tack-free, and substantially cured, it is set aside for at least seven days prior to subjecting said foam to an Oxygen Index Test, ASTM D-2863-74. The results of said test are reported in Table II.

The same procedure is used to make other foams at different load levels. These foams are also subjected to the same Oxygen Index Test (O.I.) as the above foam and the data are also reported in Table II.

TABLE II

| Flame Retardant | Load Level, php | O.I., % |
|---|---|---|
| Control | 0 | 21.0 |
| Compound 1 of Table I | 10 | 23.5 |
| Compound 1 of Table I | 20 | 25.0 |
| Compound 1 of Table I | 30 | 26.0 |
| Compound 9 of Table I | 30 | 25.0 |
| Compound 12 of Table I | 30 | 26.5 |

EXAMPLE 6

A polyester resin is prepared by mixing in a reaction vessel 148.12 grams of phthalic anhydride, 98.06 grams of maleic anhydride, 89.38 grams of ethylene glycol, 53.06 grams of diethylene glycol. The reaction vessel is then heated at 200° C. for two hours. Thereafter the temperature is lowered to 185° C. and 93.42 grams of bis-(2,3-dibromopropyl)-2,3-dimethyl-3-hydroxypropyl phosphate are added. Heating at 185° C. is continued for two hours. At the end of this period the vessel is cooled to 130° C. During cooling 0.1 grams of methyl hydroquinone inhibitor are added. After the vessel has reached 130° C. 235.7 grams of styrene are added. The vessel is then cooled to room temperature, and a fiberglass-polyester laminate is formed containing 25.9% by weight of fiberglass. Samples of this laminate are then subjected to Oxygen Index Test, ASTM D-2863-74. The results of said test are reported in Table III.

EXAMPLE 7

A polyester resin and fiberglass-polyester laminate are prepared substantially in accordance with the procedure of Example 3 except that the flame retardant additive, bis-(2,3-dibromopropyl)-2,3-dimethyl-3-hydroxypropyl phosphate, is omitted. Samples of the laminate are subjected to Oxygen Index Test, ASTM D-2863-74. The results of said test are reported in Table III.

TABLE III

| Laminate | O.I., % |
|---|---|
| Laminate of Example 3 | 32 |
| Laminate of Example 4 | 20 |

EXAMPLE 8

The hydrolytic stability of bis-(2,3-dibromopropyl)-2,2-dimethyl-3-hydroxypropyl phosphate of Example 1, bis-(bromopropyl)-chloroethyl phosphate, tris-(2-chloroethyl) phosphate, and bis-(2,3-dibromopropyl)-2-hydroxypropyl phosphate is determined by the following procedure.

A magnetically stirred emulsion containing 4 grams of one of the above three compounds, 1 gram of an emulsifier (Emcol AM2-10C, Witco Chemical Corporation, New York, N.Y.), and 45 grams of water are heated at 100° C. for 44 hours. The acid number of the emulsion is then determined by titration with a standard potassium hydroxide solution and the results are tabulated in Table IV. A compound's acid number is inversely proportional to the hydrolytic stability of that compound, i.e., the larger a compound's acid number, the poorer will be said compound's hydrolytic stability.

As exemplified by bis(2,3-dibromopropyl)-2,2-dimethyl-3-hydroxypropyl phosphate in Table IV below, the hydrolytic stability of the compounds within the scope of this invention is unobviously better than the hydrolytic stability of close prior art compounds. This increase is hydrolytic stability possessed by the compounds within the scope of this invention has significant commercial and practical implications.

TABLE IV

| Compound | HST Number (mg KOH/g Sample) |
|---|---|
| bis-(2,3-dibromopropyl)-2,3-dimethyl-3-hydroxypropyl phosphate | 3.38 |

TABLE IV-continued

| Compound | HST Number (mg KOH/g Sample) |
|---|---|
| bis-(2,3-dibromopropyl)-2-hydroxypropyl phosphate | 19.1 |
| bis-(bromopropyl) chloro-ethyl phosphate | 9.72 |
| tris-(2-chloroethyl) phosphate | 8.7 |

EXAMPLE 9

The thermal stability of the same compounds tested in Example 8 is determined by the procedure set forth in Section 9-951, "Thermogravimetric Analyzer", of "Instruction Manual 990, Thermal Analyzer and Modules", E. I. Du Pont De Nemours and Co. (Inc.), Instrument Products Division, Wilmington, Delaware 19898. The results of the thermogravimetric analyses (TGA) of the three compounds at several different weight losses are tabulated in Table V.

As exemplified by bis(2,3-dibromopropyl)-2,3-dimethyl-3-hydroxypropyl phosphate, in Table V, compounds within the scope of formula I possess superior thermal stability than that possessed by prior art compounds.

TABLE V

| | TGA Results | | | |
|---|---|---|---|---|
| | Tris(2-chloro-ethyl)phosphate | Bis(bromopropyl)-2-chloroethyl phosphate | Bis(2,3-dibromopropyl)-2-hydroxypropyl phosphate | Bis(2,3-dibromopropyl)-2,3-dimethyl-3-hydroxy-propyl phosphate |
| 5% Weight Loss | 170° C. | 169° C. | 111° C. | 233° C. |
| 10% Weight Loss | 182° C. | 185° C. | 132° C. | 246° C. |
| 25% Weight Loss | 197° C. | 212° C. | 169° C. | 260° C. |
| 50% Weight Loss | 209° C. | 232° C. | 219° C. | 276° C. |
| 75% Weight Loss | 218° C. | 245° C. | 249° C. | 293° C. |

Based on this disclosure many other modifications and ramifications will naturally suggest themselves to those skilled in the art. These are intended to be comprehended as within the scope of this invention.

The embodiments of the invention in which an exclusive property or privilege is claimed are defined as follows:

1. A phosphate of the formula

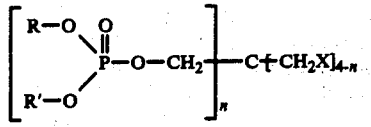

wherein R and R' are independently selected from lower haloalkyls having 2 to 6 carbon atoms and 1 to 6 halogen atoms, n is an integer from 1 to 3, and wherein each X is independently selected from hydrogen, halogen, alkyl, and hydroxyl, provided that at least one X is hydroxyl.

2. The phosphate of claim 1 wherein the halogen is chlorine or bromine.

3. The phosphate of claim 2 wherein said haloalkyls are straight chain haloalkyls.

4. The phosphate of claim 2 wherein each X is independently selected from hydrogen, halogen, and hydroxyl, provided that at least one X is hydroxyl.

5. The phosphate of claim 4 wherein said phosphate is bis(2,3-dibromopropyl)-2,2-dimethyl-3-hydroxypropyl phosphate.

6. The phosphate of claim 4 wherein said phosphate is bis-(2,3-dichloropropyl)-2,2-dimethyl-3-hydroxypropyl phosphate.

7. The phosphate of claim 4 wherein said phosphate is tetrakis(2-chloroethyl)pentaerythritoldiphosphate.

* * * * *